United States Patent
Le

(10) Patent No.: US 10,286,099 B2
(45) Date of Patent: May 14, 2019

(54) DUAL CHAMBER ULTRASONIC DIFFUSER AND METHOD OF USE

(71) Applicant: Son Le, Orem, UT (US)

(72) Inventor: Son Le, Orem, UT (US)

( * ) Notice: Subject to any disclaimer, the term of this patent is extended or adjusted under 35 U.S.C. 154(b) by 222 days.

(21) Appl. No.: 15/019,043

(22) Filed: Feb. 9, 2016

(65) Prior Publication Data

US 2017/0224864 A1  Aug. 10, 2017

(51) Int. Cl.
*A61L 9/00* (2006.01)
*A61L 9/14* (2006.01)
*B05B 17/06* (2006.01)
*B05B 7/00* (2006.01)

(52) U.S. Cl.
CPC .............. *A61L 9/14* (2013.01); *B05B 7/0075* (2013.01); *B05B 7/0081* (2013.01); *B05B 17/0684* (2013.01); *A61L 2209/132* (2013.01); *A61L 2209/133* (2013.01); *A61L 2209/134* (2013.01)

(58) Field of Classification Search
CPC ................ A61L 9/14; A61L 2209/132; A61L 2209/133; A61L 2209/134; B05B 7/0416; B05B 17/06; B05B 17/0416; B05B 17/0607

USPC ............................................................. 239/8
See application file for complete search history.

(56) References Cited

U.S. PATENT DOCUMENTS

| | | | | |
|---|---|---|---|---|
| 4,752,422 A * | 6/1988 | Uchida | ................... | A61L 9/122 239/58 |
| 4,816,973 A * | 3/1989 | Atalla | ..................... | F21S 8/035 362/101 |
| 6,196,527 B1 * | 3/2001 | Huang | ...................... | A61L 9/03 261/142 |
| 8,544,826 B2 * | 10/2013 | Ediger | ...................... | F24F 6/12 261/30 |
| 8,827,247 B2 * | 9/2014 | Kanel | ....................... | F24F 6/02 261/29 |
| 2005/0199740 A1 * | 9/2005 | Harris, Jr. | ........... | A01M 1/2044 239/34 |
| 2013/0334336 A1 * | 12/2013 | Haran | ...................... | A61L 9/14 239/4 |

\* cited by examiner

*Primary Examiner* — Viet Le

(74) *Attorney, Agent, or Firm* — Workman Nydegger

(57) ABSTRACT

A dual chamber ultrasonic essential oil diffuser or nebulizer or more specifically to a diffuser having a reservoir or first chamber specifically for distilled water, a second air transfer chamber having a replaceable aroma cartridge and the diffuser being capable of mixing the nebulized water mist and essential oil aroma away from the transducer.

20 Claims, 4 Drawing Sheets

DUAL CHAMBER ULTRASONIC DIFFUSER AND METHOD OF USE

BACKGROUND

During recent years there has been a high demand for home use diffusers configured to displace aromatic essential oils into the environment. Advocates for the industry tout the benefits of the essential oils beyond the aromatic quality and argue that the oils have properties that clean the air, killing bacteria and viruses, reduce the effects of a sickness, relieve stress, promote sleep, and numerous other positive attributes.

A typical diffuser or nebulizer includes a piezo transducer within a fluid reservoir and possibly a fan to more widely disperse the mist. Basic use of the diffuser includes, filing the reservoir with distilled water and then adding a few drops of an essential oil of choice directly into the water. Most thin oils will disperse fairly evenly throughout the reservoir and will be nebulized with the water to create an aromatic mist. The user may add more essential oil to the reservoir if a stronger aroma is desired.

While the process of using a typical diffuser is fairly simple, this arrangement does have limitations, including, but no limited to, difficulty changing from one aroma to another, the choice of oil is limited to thin or low viscosity oils, required cleaning of the transducer, and regular transducer failure.

If a user desires to change from one essential oil aroma to another, the user must move the unit to a sink or drain where the water can be poured from the reservoir and then the user must wipe down the inside of the reservoir in order to remove any residual oil film from the walls. Any oil that is left in the reservoir will contaminate the aroma of the next oil chosen and may damage the transducer. Once the reservoir is wiped, the user can refill the reservoir with distilled water and add drops of a new desired essential oil aroma and replace the diffuser to a location before restarting.

A user may desire to use an essential oil that has a thicker consistency or viscosity however; most thick oils will have a propensity to stay together in single mass or drop and will not disperse into the water. In this condition the oil will not be nebulized with the water and may damage the transducer once all of the reservoir water is used.

The typical diffuser also requires considerable maintenance for best efficiency and to protect the transducer. Some manufactures will require that the foil surface of the transducer is swabbed to remove oil and mineral residue after each use, others recommend soaking the transducer in a mild acid solution, such as citric acid or white vinegar in order to clean the surface of the transducer. When the transducer is not maintained, oil residue and mineral deposited will build up and the transducer will no longer efficiently nebulize water and may ultimately overheat and fail.

Other issues that may occur with a traditional diffuser includes the water and oil not being fully, or finely, nebulized, causing the water mist to fall quickly, coating the surface where the diffuser is placed with water and causing an essential oil build up on the surface. This condition may damage a counter top or the furniture where a diffuser is routinely placed. Additionally, the plastic parts on some diffusers will degrade from exposure to the essential oil; this may cause the plastic parts to change color, become tacky or brittle.

What is needed is a diffuser or nebulizer that creates a fine water mist, allows a user to easily change from one essential oil aroma to another, which can use any volatile oil regardless of thickness or viscosity, which is easy to maintain and is reliable.

SUMMARY OF THE INVENTION

The disclosure of the present invention relates to a dual chamber ultrasonic essential oil diffuser or nebulizer, or more specifically to a diffuser having a reservoir or chamber specifically for distilled water, a second chamber having a replaceable aroma cartridge and the diffuser being capable of mixing the nebulized water mist and essential oil aroma away from the transducer.

One embodiment of the present invention or dual chamber ultrasonic diffuser includes as core components, an ultrasonic piezo transducer, a distilled water reservoir as a first chamber and aroma dispersion assembly isolated in a second independent chamber. The distilled water reservoir serves as the base of the unit and is configured to mate with a cylindrical external housing. The housing having two openings on the upper most surface, the ultrasonic piezo transducer attached within the first opening, and an aroma cartridge is configured to be inserted within the second opening. The ultrasonic transducer is electronically connected to a printed circuit board or PCB through a switching element. The transducer is located above the distilled water reservoir in order to provide optimal nebulizing or misting effect and to physically protect the transducer. Water from the reservoir is moved to the transducer using a columnar wicking element; the wicking element is made using a fibrous material such as polyester or polypropylene. The aroma cartridge includes a rigid frame assembly configured to support a fibrous felt element which is saturated with an essential oil. The support frame also includes a pull tab or finger tab for ease of installation and to protect the user from the essential oil within the saturated felt. The aroma cartridge configured to be inserted into the second opening or second chamber where a small fan is used to drive air through the saturated felt and to dissipate the volatile aroma component of the essential oil. The air from the second chamber is directed toward the first opening and is introduced into the stream of nebulized water mist from the transducer. The upward velocity of the water mist stream creates a low pressure column of air with a rotational component that draws in and thoroughly mixes the essential oil volatile aroma particles with the water mist. It is contemplate that the diffuser will be sold with a plurality of aroma cartridges, allowing a user to dose the individual cartridges with an essential oil and readily change aroma by inserting a different cartridge. A compartmentalized storage container may also be provided to allow long term individual storage of the cartridges and reduce the chance of cross contaminating aromas. A user can remove a desired aroma cartridge from the storage container, dose the felt with fresh oil and insert the cartridge into the diffuser housing. In another embodiment the aroma cartridges may be provided as individually foil wrapped elements that are preloaded with a desired essential oil. In yet another embodiment, the diffuser is configured to allow as user to selectively choose between operating as a water nebulizer or an aroma diffuser. A user may choose to operate the unit in a humidifier mode without any aroma or operate the unit as an aroma diffuser without the water mist.

Another embodiment of the present invention is configured having at least a third opening or at least a third chamber configured to receive another aroma cartridge.

In another embodiment of the present invention, the diffuser includes the capacity to blend the nebulized water mist from the first chamber and the aroma from a second chamber, or from more than a second chamber, within an exhaust vent or mixing chamber formed integral with the diffuser. In yet another embodiment, the diffuser may include a cap or cover having an intake vent than aligns with the piezo transducer in the first chamber and at least a second intake vent that aligns with the discharge from at least one aroma chamber. The flow from the respective intakes, blending in a mixing chamber, or in an exhaust chamber, before discharging through an exhaust vent on the cover.

One embodiment of the present invention is configured having a reservoir and external housing sized to be portable and may be moved from home, to office and within a personal vehicle. The diffuser is configured to use transformed 110 AC household voltage, or DC voltage, from a source such as a USB output from a computer or car. The power supply may also be configured to attach directly into a cigarette lighter still available in some older vehicles. In one embodiment the diffuser is sized to fit securely within a cup holder of a vehicle and the power supply cable is located near the top of the diffuser housing to allow clearance between the cup holder and the power supply cable. The distilled water reservoir may also include a sealing mechanism to prevent spillage when using the diffuser in a vehicle.

Another embodiment of the present invention the diffuser distilled water reservoir and housing are configured in a large size to optimize run time without refilling the reservoir.

In another embodiment of the present invention a resistance based level sensor will be included within the distilled water reservoir. The level sensor configured to sense a low water level and shut down the diffuser through the PCB in order to protect the transducer from operating in a dry environment, overheating and possibly failing.

In yet another embodiment the top cover, the aroma cartridge and, possibly other components, are manufactured using a fluorinated plastic formulated to resist degradation from exposure to the essential oil.

BRIEF DESCRIPTION OF DRAWINGS

The following description of the embodiments can be understood in light of the Figures which illustrate specific aspects of the embodiments and are part of the specification. Together with the following description, the Figures demonstrate and explain the principles of the embodiments. In the Figures the physical dimensions of the embodiment may be exaggerated for clarity. The same reference numerals or word descriptions in different drawings represent the same element, and thus their descriptions may be omitted.

Figure 1:
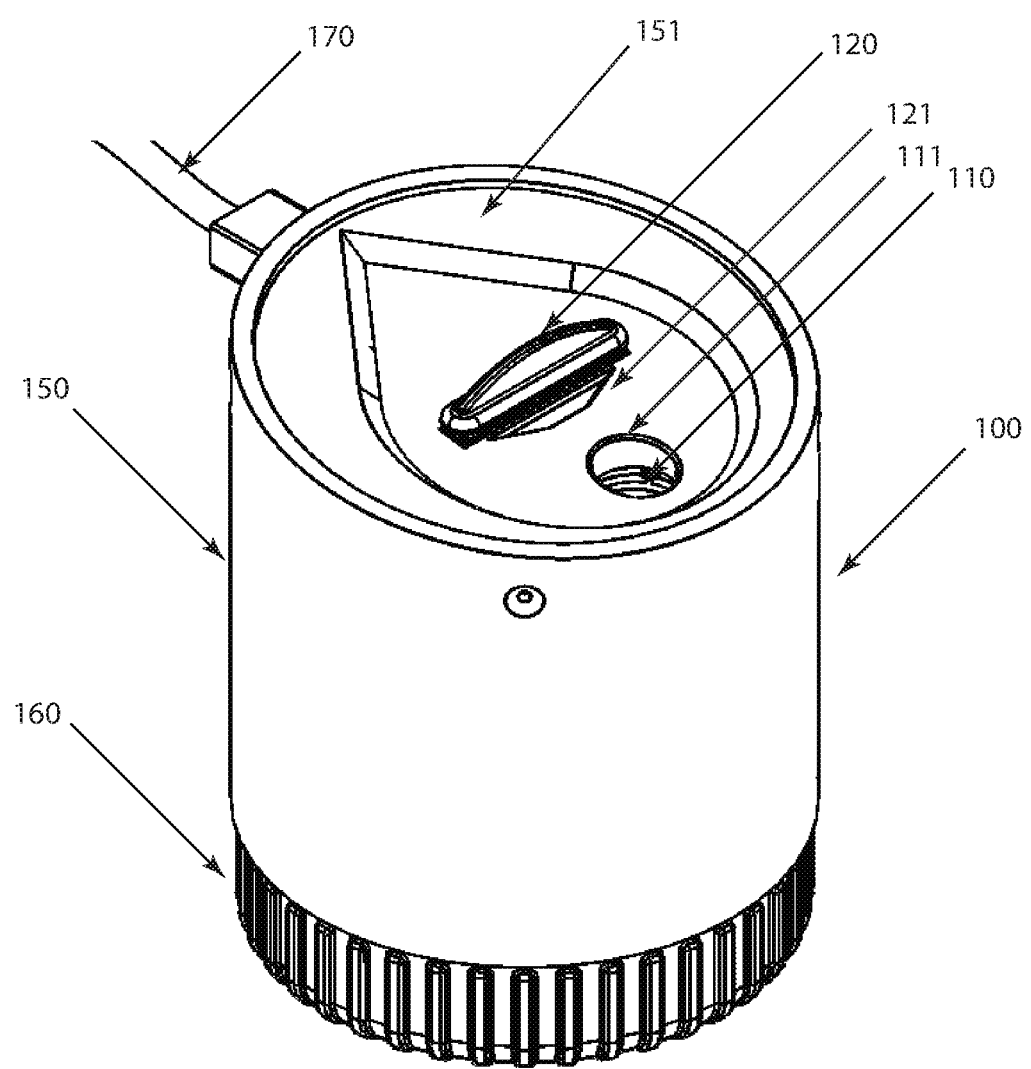
FIG. 1 is a perspective view of a dual chamber ultrasonic diffuser.

It is to be understood that the above mentioned arrangements are only illustrative of the application of the principles of the present disclosure. Numerous modifications or alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

DETAILED DESCRIPTION OF THE DRAWINGS

FIG. 1 is a dual chamber ultrasonic diffuser 100, including a reservoir base 160, a substantially cylindrical external housing 150 with a top cover 151 fitted to the external housing 150. The top cover having a first nebulizer opening 111 including a piezo transducer 110 located at the bottom of the nebulizer opening, a second aroma opening 121 configured to receive a aroma cartridge 120; the aroma opening 121 including a louver that directs air flow toward the nebulizer opening 111. A USB power supply 170 is configured to electrically connect to the diffuser external housing 150 near the top cover 151.

Figure 2:
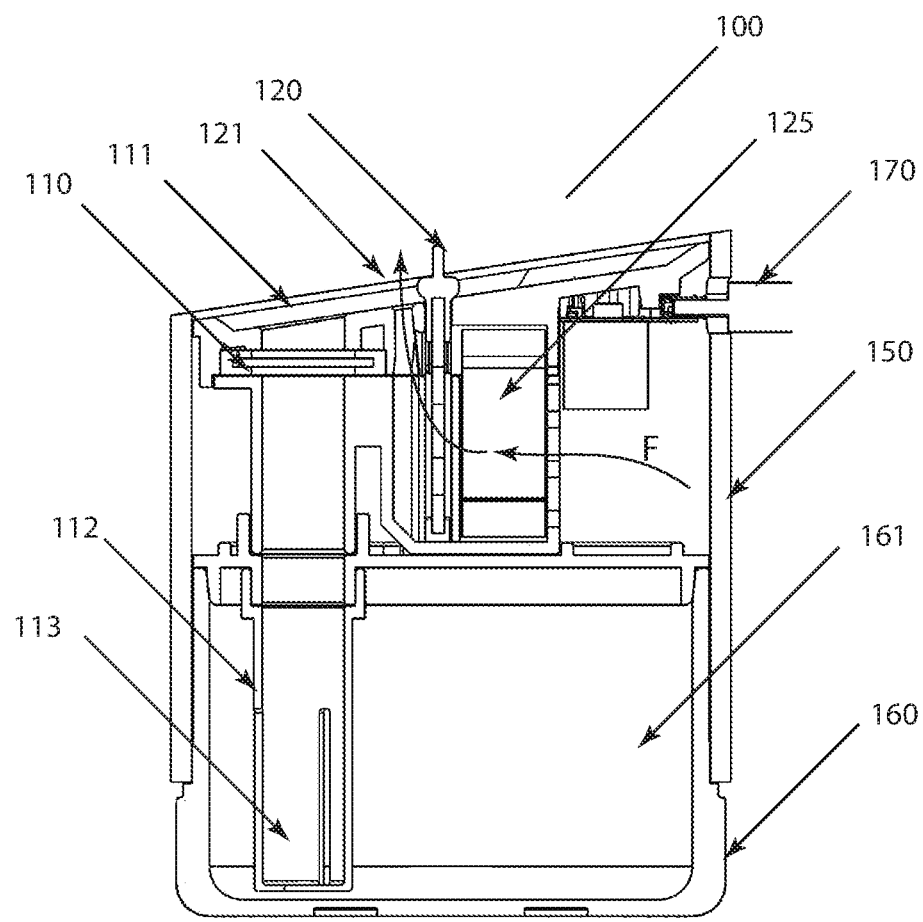
FIG. 2 is an exploded view of a dual chamber ultrasonic diffuser.
Figure 3:
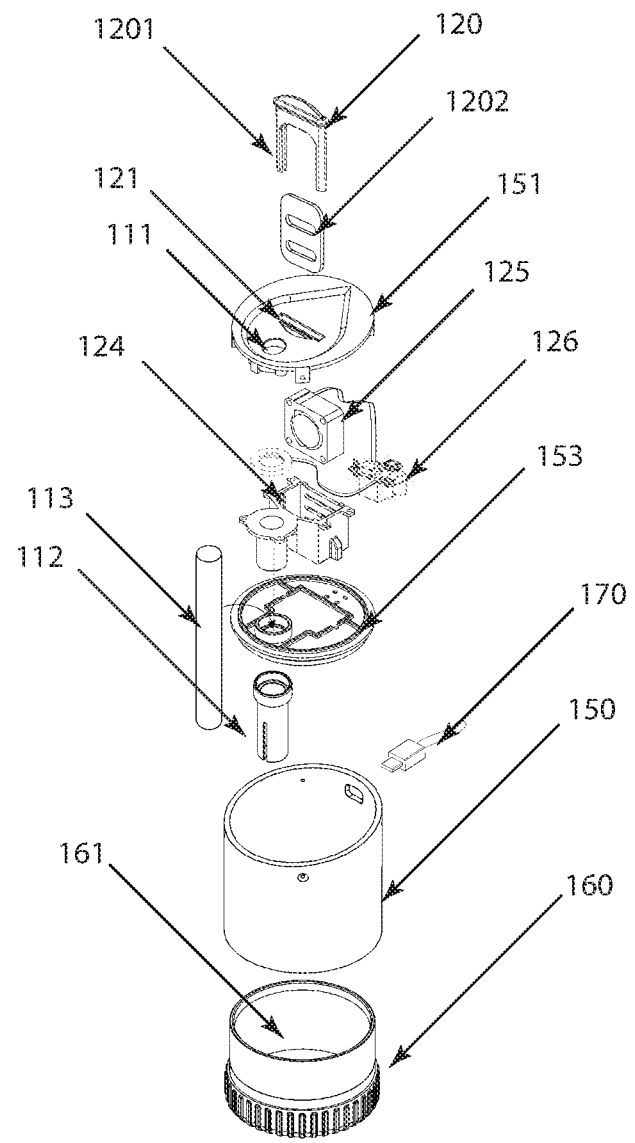
FIG. 3 is a section view of a dual chamber ultrasonic diffuser.
Figure 4:
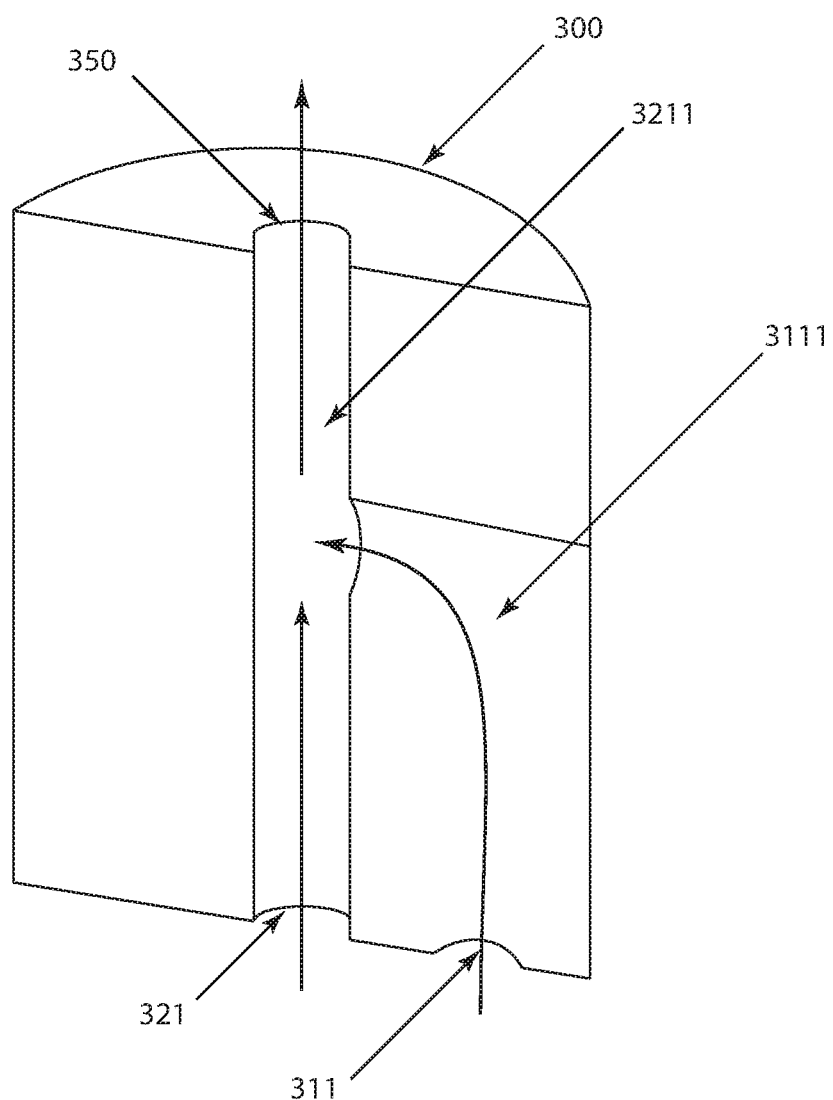
FIG. 4 is a section view of a blending cover for a diffuser.

FIGS. 2 and 3 of diffuser 100 include additional internal details such as the distilled water reservoir 161, a wicking element housing 112 and a wicking element 113 used to move distilled water to the piezo transducer 110. A reservoir cap 153 is configured to isolate internal electronic elements from the distilled water stored within the water reservoir 161. In yet another embodiment a seal, not shown, is configured between the reservoir base 160 and external housing 150. A lower housing 152 is configured to support the wicking element housing 112, a PCB 126, and a fan 125 within an air transfer chamber 124. The aroma cartridge 120 including a rigid frame portion 1201 and a fibrous felt portion 1202.

Operation of the diffuser 100 is best shown in FIG. 2; water from the distilled water reservoir 161 is drawn to transducer 110 via the wicking action of molecular attraction where it is nebulized into a fine water mist column. Air driven by fan 125 is forced through the felt portion 1202, which is saturated with essential oil, of aroma cartridge 120 and out the second aroma opening 121. The air from opening 121 is directed into the fine water mist column emitted from the nebulizer opening 111. The volatile aroma of the essential oil is thoroughly mixed with, and bonds to, the water particles of the mist column and the aroma of the essential oil is disseminated throughout the environment.

FIG. 4 shows a cover 300 configured to fit over the diffuser 100 of the present invention. Cover 300 includes a nebulizer mist intake 311, a mist passage 3111, an aroma intake 321, and an aroma passage 3211. Mist from intake 311 will blend with aroma traveling in aroma passage 3211 and will discharge from the diffuser cover 300 through an exhaust vent 350.

The invention claimed is:

1. A dual chamber ultrasonic diffuser comprising, a housing;

a water reservoir;

a first chamber disposed within the housing and in fluid communication with the water reservoir, the first chamber associated with a transducer configured to nebulize water from the water reservoir to water mist, the water mist discharging from a water mist opening of the first chamber;

a second chamber disposed within the housing and isolated from the first chamber;

an aroma cartridge disposed within the second chamber and comprising a rigid frame and an aroma felt connected to a portion of the rigid frame;

a fan associated with the second chamber and configured to push air flow through the aroma cartridge, wherein the air flow is discharged out of an aroma opening of the second chamber, and wherein the air flow blends with the water mist at an area outside of the housing.

2. The diffuser of claim 1, comprising a wick assembly, the wick assembly communicating water to the transducer.

3. The diffuser of claim 1, wherein the aroma cartridge comprises a cavity formed by the rigid frame and the aroma felt such that the air flow from the fan passes through the aroma felt and into the cavity and is directed by the rigid frame to the opening of the second chamber.

4. The diffuser of claim 3 wherein the rigid frame is comprised of a fluorinated plastic.

5. The diffuser of claim 1, further comprising a top cover comprised of a fluorinated plastic.

6. The diffuser of claim 1, wherein the housing is configured to fit into a vehicle cup holder.

7. The diffuser of claim 6, comprising a power supply cable configured to mate with the housing at a position on the housing above a vertical wall of the vehicle cup holder.

8. The diffuser of claim 1 wherein the transducer and fan are controlled by a printed circuit board.

9. The diffuser of claim 8 wherein the transducer and the fan are operated independently.

10. The diffuser of claim 1, further comprising a power supply selected from one of household current or low voltage direct current.

11. A method of using a dual chamber ultrasonic diffuser comprising:
providing the dual chamber ultrasonic diffuser of claim 1;
adding distilled water to the water reservoir;
removing the aroma cartridge from the second chamber;
applying a first essential oil to the aroma cartridge;
replacing the aroma cartridge into the second chamber;
nebulizing the distilled water from the water reservoir to form the water mist, the water mist being discharged from the water mist opening of the first chamber;
activating the fan to push air flow through the first aroma cartridge, the air flow being discharged out of the aroma opening of the second chamber, wherein the air flow blends with the water mist at an area outside of the housing.

12. The method of claim 11, further comprising:
removing the aroma cartridge from the second chamber;
selecting a second aroma cartridge;
applying a second essential oil to the second aroma cartridge; and
installing the second aroma cartridge into the second chamber.

13. The diffuser of claim 1, further comprising a sealing mechanism associated with the water reservoir to prevent spillage.

14. The diffuser of claim 1, further comprising a level sensor configured to sense a water level in the water reservoir.

15. The diffuser of claim 1, further comprising a louver associated with the aroma opening of the second chamber, the louver being configured to direct the discharged air flow toward the discharged water mist.

16. The diffuser of claim 1, further comprising:
an additional aroma chamber disposed within the housing and isolated from the first chamber; and
an additional aroma cartridge disposed within the additional aroma chamber,
wherein air flow from the fan or an additional fan associated with the additional aroma chamber passes through the additional aroma cartridge and is discharged to an area outside of the housing.

17. The diffuser of claim 1, further comprising a cover configured to associate with the housing, the cover comprising:
an exhaust vent;
a water mist intake defined by the cover to align with water mist opening;
a water mist passage defined between the exhaust vent and the water mist intake;
an aroma intake defined by the cover to align with the aroma opening; and
an aroma passage defined between the aroma intake and the water mist passage.

18. The diffuser of claim 1, wherein the cover is configured to discharge an aromatic blend from the exhaust vent, the aromatic blend comprising the water mist and the air flow.

19. A kit, comprising:
the dual chamber ultrasonic diffuser of claim 1; and
a plurality of aroma cartridges configured for use with the diffuser.

20. The kit of claim 19, further comprising a power supply.

* * * * *